(12) United States Patent
Garssen et al.

(10) Patent No.: US 7,566,543 B2
(45) Date of Patent: *Jul. 28, 2009

(54) PRION TEST

(75) Inventors: Gerrit Jan Garssen, Driebergen (NL); Jorg Günther Jacobs, Lelystad (NL); Joannes Pieter M. Langeveld, Harderwijk (NL); Marinus Adrianus Smits, Harderwijk (NL); Lucien Johannes M. van Keulen, Oudemirdum (NL); Bram Edward C. Schreuder, Lelystad (NL); Alexander Bossers, Lelystad (NL)

(73) Assignee: ID-Lelystad, Instituut Voor Dierhouderij en Diergezonheid B.V., Lelystad (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/977,089

(22) Filed: Oct. 22, 2007

(65) Prior Publication Data
US 2008/0153117 A1 Jun. 26, 2008

Related U.S. Application Data

(63) Continuation of application No. 09/913,345, filed as application No. PCT/NL00/00079 on Feb. 9, 2000, now Pat. No. 7,344,842.

(30) Foreign Application Priority Data
Feb. 11, 1999 (EP) .................................. 99200391

(51) Int. Cl.
*G01N 33/53* (2006.01)
*G01N 1/30* (2006.01)
*A61K 39/395* (2006.01)
*A61K 39/00* (2006.01)

(52) U.S. Cl. ....................... 435/7.1; 435/40.5; 530/300; 530/350; 424/130.1; 424/139.1; 424/184.1

(58) Field of Classification Search .............. 424/130.1, 424/139.1, 184.1; 435/7.1, 40.5; 530/300, 530/350
See application file for complete search history.

(56) References Cited

U.S. PATENT DOCUMENTS

| 4,806,627 | A | 2/1989 | Wisniewski et al. |
| 5,565,186 | A | 10/1996 | Prusiner et al. |
| 6,150,172 | A | 11/2000 | Schmerr et al. |
| 7,344,842 | B1 * | 3/2008 | Garssen et al. ............... 435/7.1 |

FOREIGN PATENT DOCUMENTS

| WO | WO 93/23432 | 11/1993 |
| WO | WO 97 10505 | 3/1997 |
| WO | WO 97/37227 | 10/1997 |
| WO | WO 98 32334 | 7/1998 |
| WO | WO 99/19360 | 4/1999 |
| WO | WO 00/48003 | 8/2000 |

OTHER PUBLICATIONS

Bell et al, "Prion Protein Immunocytochemistry—UK Five Centre Consensus Report," Neuropathology and Applied Neurobiology, 1997, 23, 26-35.
Belt et al., Identification of the five allelic variants of the sheep PrP gene and their association with natural scrapie, Journal of General Virology, 1995, pp. 1-10.
Brown, Can Creutzfeldt-Jakob disease be transmitted by transfusion? 1995, pp. 472-477, Rapid Science Publishers.
Diringer et al., Scrapie infectivity, fibrils and low molecular weight protein, Nature, Dec. 1983, 476-78, Macmillan Journals Ltd.
Doi et al., "Western Blot Detection of Scrapie-associated Fibril Protein in Tissues outside the Central Nervous System from Preclinical Scrapie-infected Mice," *J. Gen. Virol*, 69, pp. 955-960, 1988.
Fraser et al., Transmission of bovine spongiform encephalopathy to mice, Journal of Small Animal Practice, 1988, p. 565, vol. 29.
Fraser, Murine Scrapie Strains, BSE Models and Genetics, Sub-acute Spongiform Encephalopathies, pp. 131-136, the Netherlands, 1991.
Fraser et al., Studies of the Lymphoreticular System in the Pathogenesis of Scrapie: The Role of Spleen and Thymus, J. Comp. Path., 1978, pp. 563-573, vol. 88.
Grathwohl et al., "Sensitive enzyme-linked immunosorbent assay for detection of PrP in crude tissue extracts from scrapie-affected mice," Journal of Virological Methods, vol. 64, pp. 205-216, 1997.
Hadlow et al., Natural Infection of Suffolk Sheep with Scrapie Virus, The Journal of Infectious Diseases, Nov. 1982, pp. 657-664.
Hadlow et al., "Virologic and Neurohistologic Findings in Dairy Goats Affected with Natural Scrapie," *Vet. Pathol.* 17, pp. 187-199, 1980.
Henri et al., Recherche d'un temoin biochimique urinaire de l'infection du mouton par la tremblante, Bulletin de L'academie Veterinaire de France, pp. 139-145, 1992.
Hilmert et al., A rapid and efficient method to enrich SAF-protein from scrapie brains of hamsters, Bioscience Reports, 1984, pp. 165-170, vol. 4.
Ikegami et al. "Pre-clinical and clinical diagnosis of scrapie by detection of PrP protein in tissues of sheep," *The Veterinary Record*, pp. 271-275, Mar. 23, 1991.
Korth et al., "Prion (PrP$^{Sc}$)-specific epitope defined by a monoclonal antibody," *Nature*, vol. 390, pp. 74-75, 1997.
Meiner et al., Presence of prion protein in peripheral tissues of Libyan Jews with Creutzfeldt-Jakob disease, Neurology, Jul. 1992, pp. 1355-1360, vol. 42.
Mohri et al., Immunodetection of a disease specific PfP fraction in scrapie-affected sheep and BSE-affected cattle, Veterinary Record, 1992, pp. 537-539, vol. 131.

(Continued)

*Primary Examiner*—Rodney P. Swartz
(74) *Attorney, Agent, or Firm*—TraskBritt

(57) ABSTRACT

The invention is related to diagnostic methods for detecting transmissible spongiform encephalopathies (TSEs) such as BSE and scrapie and related disease in humans. The invention provides use of guanidine thiocyanate (gdnSCN), or a functional equivalent thereof, for treating at least one sample derived from a mammal, including humans, for reducing the risk of scoring a false-positive test result in testing the sample for the presence or absence of aberrant prion protein.

11 Claims, 4 Drawing Sheets

OTHER PUBLICATIONS

Muramatsu et al. "Detection of PrP$^{Sc}$ in sheep at the preclinical stage of scrapie and its significance for diagnosis of insidious infection," *Arch Virol*, 134, pp. 427-432, 1993.

Muramoto et al., Accumulation of Abnormal Prion Protein in Mice Infected with Creutzfeldt-Jakob Disease via Intraperitoneal Route: A Sequential Study, American Journal of Pathology, Nov. 1993, pp. 1470-1479, vol. 143, No. 5.

Oesch et al., "Properties of the Scrapie Prion Protein: Quantitative Analysis of Protease Resistance," Biochemistry, 1994, 33, 5926-5931.

O'Rourke et al. "Monoclonal Antibody F89/160.1.5 Defines a Conserved Epitope on the Ruminant Prion Protein," *Journal of Clinical Microbiology*, vol. 36, No. 6, pp. 1750-1755, Jun. 1998.

O'Rourke et al. "Preclinical detection of PrP$^{Sc}$ in nictitating membrane lymphoid tissue of sheep," *The Veterinary Record*, pp. 489-491, May 2, 1998.

Schreuder, Animal Spongiform Encephalopathies—An Update, Part I. Scrapie and Lesser Known Animal Spongiform Encephalopathies, Veterinary Quarterly, Oct. 1994, pp. 174-181, vol. 16, No. 3.

Schreuder, Animal Spongiform Encephalopathies—An Update, Part II. Bovine Spongiform Encephalopathy (BSE), Veterinary Quarterly, Oct. 1994, pp. 182-192, vol. 16, No. 3.

Schreuder et al., "Tonsillar biopsy and PrP$^{Sc}$ detection in the preclinical diagnosis of scrapie," *Papers and Articles*, pp. 1-9, Apr. 15, 1998.

Shinagawa et al. "Immunoreactivity of a Synthetic Pentadecapeptide Corresponding to the N-Terminal Region of the Scrapie Prion Protein," *J. Gen. Virol.* 67, pp. 1745-1750, 1986.

Van Keulen et al., Immunohistochemical Detection and Localization of Prion Protein in Brain Tissue of Sheep with Natural Scrapie, Vet Pathol, 1995, pp. 299-308, vol. 32.

\* cited by examiner

```
  1 hu  M A - - N L G C W M L V L F V A T W S D L G L C K K R P K P -   28
  1 rb  - - H     Y       L           V             G                 29
  1 ha        S Y   L   A         M T V               -                28
  1 mo        G Y   L   A       T M T V               -                28
  1 bo  V K S H I   S   I         M   V             G                  31
  1 ov  V K S H I   S   I         M   V             G                  31

G
 29 hu  G G W N T G S R Y P G Q G S P G G N R Y P P Q G G G W G Q P   60
 30 rb                        S                                       60
 29 ha                                                    T            60
 29 mo                                                  T              59
 32 bo                                                                 63
 32 ov                                                                 63

61 hu  H G G G W G Q P H G G G W G Q P H G G G W G Q P H G G - W G   90
 61 rb                                                          -     90
 61 ha                                                          -     90
 60 mo                S                 S                       -     89
 64 bo                                                          G     94
 64 ov                                                          G     94

G              L   L         F             V
 91 hu  Q G G G T H S Q W N K P S K P K T N M K H M A G A A A A G A  120
 91 rb          -     N     G             S       V                  119
 91 ha                N                           M                  120
 90 mo                N                       L   V                  119
 95 bo          -     G                           V                  123
 95 ov          - S                               V                  123

V     V T       F                   V
121 hu  V V G G L G G Y M L G S A M S R P I I H F G S D Y E D R Y Y  150
120 rb                                  L         N                  149
121 ha                              M M           N   W              150
120 mo                    M         M             N   W              149
124 bo                              L                                153
124 ov                              L             N                  153

H           .           Q                 N   I
151 hu  R E N M H R Y P N Q V Y Y R P M D E Y S N Q N N F V H D C V  180
150 rb        Y                     V Q               S              179
151 ha        N                     V Q       N                      180
150 mo        Y                     V Q                              179
154 bo                              V Q                              183
154 ov        Y                     V R                              183

V             S K               I
181 hu  N I T I K Q H T V T T T T K G E N F T E T D V K M M E R V V  210
180 rb        V                                       I I            209
181 ha                                                I I            210
180 mo              T                                                209
184 bo        V   E                                   I              213
184 ov        V                                       I I            213

R                               R
211 hu  E Q M C I T Q Y E R E S Q A Y Y - Q R G - S S M - V - L F S S P P V  240
210 rb              Q Q       A   -     - A - A G - L                        239
211 ha      T       Q K           D G R - S   A -                            241
210 mo  V           Q K           D G R -     S T -                          241
214 bo              Q             -             A - - - I                    243
214 ov              Q                           A - - - I                    243

241 hu  I L L I S F L I F L I V G   253
240 rb                              252
242 ha                      M       254
242 mo                              254
244 bo                              256
244 ov                              256
```

Amino acid sequences of human, rabbit, hamster, mouse, cattle and sheep PrP genes. The entire amino acid sequence of human PrP is given; open spaces in the other sequences indicate identity. Polymorphisms are indicated in bold at the top of each block and relate to the shaded positions. ↓: PHGGGWGQ. |: protease-sensitive site, right of which the sequence for the PK-resistant core of PrP$^{sc}$ is found. The mature PrP is devoid of N and C terminal signal peptides (in huPrP: amino acids 1-22 and 232-253, respectively).

FIG. 1

Rabbit antipeptide antisera to parts of the ovine PrP-structure

R521, R522 (to ovine sequence 94-105)

| | | | | | | | | | | | | | | |
|---|---|---|---|---|---|---|---|---|---|---|---|---|---|---|
| 90 | hu | G | Q | G | G | G | T | H | S | Q | W | N | K | P |
| 90 | rb | G | | | | - | | | N | | | G | | |
| 90 | ha | G | | | | | | | N | | | | | |
| 89 | mo | G | | | | | | | N | | | | | |
| 94 | bo | G | | | | - | | | G | | | | | |
| 94 | ov | G | | | | - | S | | | | | | | |

R504, R505, R593-596 (100-111)

| | | | | | | | | | | | | | |
|---|---|---|---|---|---|---|---|---|---|---|---|---|---|
| 97 | hu | S | Q | W | N | K | P | S | K | P | K | T | N |
| 96 | rb | N | | | G | | | | | | | | S |
| 97 | ha | N | | | | | | | | | | | |
| 96 | mo | N | | | | | | | | | | | |
| 100 | bo | G | | | | | | | | | | | |
| 100 | ov | | | | | | | | | | | | |

***R568* (126-143)**

| | | | | | | | | | | | | | | | | | | | |
|---|---|---|---|---|---|---|---|---|---|---|---|---|---|---|---|---|---|---|---|
| 123 | hu | G | G | L | G | G | Y | M | L | G | S | A | M | S | R | P | I | I | H |
| 122 | rb | | | | | | | | | | | | | | | | L | | |
| 123 | ha | | | | | | | | | | | | | | | | M | M | |
| 122 | mo | | | | | | | | | | | | M | | | | M | | |
| 126 | bo | | | | | | | | | | | | | | | | L | | |
| 126 | ov | | | | | | | | | | | | | | | | L | | |

***R532* (145-177)**

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| 142 | hu | G | S | D | Y | E | D | R | Y | Y | R | E | N | M | H | R | Y | P | N | Q | V | Y | Y | R | P | M | D | E | Y | S | N | Q | N | N |
| 141 | rb | | N | | | | | | | | | | | | Y | | | | | | | | | | | V | | Q | | | | | | S |
| 142 | ha | | N | | W | | | | | | | | | | N | | | | | | | | | | | V | | Q | | N | | | | |
| 141 | mo | | N | | W | | | | | | | | | | Y | | | | | | | | | | | V | | Q | | | | | | |
| 145 | bo | | | | | | | | | | | | | | | | | | | | | | | | | V | | Q | | | | | | |
| 145 | ov | | N | | | | | | | | | | | | Y | | | | | | | | | | | V | | R | | | | | | |

***R523, R524* (223-234)**

| | | | | | | | | | | | | | | |
|---|---|---|---|---|---|---|---|---|---|---|---|---|---|---|
| 220 | hu | R | E | S | Q | A | Y | Y | - | Q | R | G | - | S |
| 219 | rb | Q | | | | | A | | - | | | - | A | - |
| 220 | ha | K | | | | | | | D | G | | R | - | S |
| 219 | mo | K | | | | | | | D | G | | R | - | |
| 223 | bo | | | | | | | | - | | | | A | |
| 223 | ov | | | | | | | | - | | | | A | |

FIG. 2

Example of test result with brain-stem extract from sheep

PRION TEST

CROSS-REFERENCE TO RELATED APPLICATIONS

This application is a continuation of U.S. patent application Ser. No. 09/913,345, filed Mar. 25, 2002, U.S. Pat. No. 7,344,842, which application was a national phase entry under 35 U.S.C. § 371 of International Patent Application No. PCT/NL00/00079, filed Feb. 9, 2000, published in English as International Patent Publication WO 00/48003 on Aug. 17, 2000, which claims priority to European Patent Application No. EP 99200391.3, filed Feb. 11, 1999, the contents of each of which are incorporated herein by this reference.

TECHNICAL FIELD

The invention is related to diagnostic methods for detecting transmissible spongiform encephalopathies (TSEs) such as BSE, scrapie and related diseases in animals and humans.

BACKGROUND

Bovine spongiform encephalopathy (BSE or mad cow disease) of cattle and scrapie of sheep are fatal, non-inflammatory neurodegenerative diseases caused by prions and are characterized by a long incubation period. In humans, Creutzfeldt-Jakob disease (CJD), Gerstmann-Straussler-Scheinker syndrome (GSS), fatal familial insomnia and kuru belong to this category of TSEs.

Although scrapie, the prototype of the family of TSEs, in sheep and goats has been known for over 200 years (Pattison, 1988) and has been diagnosed world-wide (with the exception of New Zealand and Australia), it is only since 1986 that BSE has been described in cattle in the UK. By Jan. 1998, there had been 170,259 confirmed cases of BSE in Great Britain and there may exist a great number of cases of not yet overt ("silent") BSE. BSE probably emerged because scrapie-contaminated sheep offal had been included in cattle feeding-stuff via meat and bone meal and newly infected cattle material was then recycled (Wilesmith et al., 1991). This mechanism is quite plausible since ovine scrapie could be transmitted experimentally to several animal species, including cattle (Hourrigan, 1990; Gibbs, 1990).

Alternatively, recycling of offal from a rare case of spontaneous BSE for cattle feedstuff could also have led to the BSE epidemic. Moreover, the number of cattle in the UK with BSE reported annually is declining after the ban on feeding meat and bone meal in 1988.

Brain homogenates from cows with BSE produce, after inoculation of mice, a characteristic pattern of brain lesions in mice. Also, characteristic incubation periods in inbred lines of mice are seen. This is identical to the pattern elicited by brain tissue from individuals who recently have died from new-variant Creutzfeldt-Jakob disease (nvCJD; Bruce, 1997). The conclusion is that the BSE agent is identical to the nvCJD agent. Through 1996, this variant has caused the death of 35 young Britons and one Frenchman (Will et al., 1996).

There is also concern that the BSE strain that seems to be transmissible to humans may have infected sheep, where it could produce a disease hardly distinguishable from scrapie. When its ominous strain-specific properties are maintained across the species barrier, sheep BSE may be a threat to human health, although scrapie by itself does not seem to transmit to humans. Indeed, BSE agent has been transmitted experimentally to sheep by the oral route (Foster et al., 1993) and thus could have the potential to infect sheep under field conditions. With the exception of a bioassay in mice, no diagnostic method is available to discriminate between BSE and scrapie in sheep at present.

Thus far, the only known component of the infectious prion is an abnormal, disease-causing isoform of the "normal" prion protein (PrP) called $PrP^{Sc}$ or aberrant prion protein. PrP, or normal prion protein, is ubiquitous in mammalian cells in a benign, cellular conformation ($PrP^{C}$) and is encoded within a single exon as a protein of about 250 amino acid residues (FIG. 1) (SEQ ID NOS:1-6). The PrP gene has been cloned and sequenced from a variety of species, and there is a high degree of structural and organizational homology between mammalian PrP sequences (Schatzl et al., 1995). PrPs in many mammals have a 22-24-residue long N-terminal signal sequence as well as a 22-24-residue long C-terminal signal sequence for attachment of a GPI-anchor. This glycosylphosphatidylinositol linkage is a fairly common means of anchoring proteins to membranes of eukaryotic cells. Further structural characteristics of the mature protein (of 206-210 amino acid residues) are one disulfide bond and two sites for Asn-linked glycosylation.

$PrP^{Sc}$ originates from the normal cellular isoform ($PrP^{C}$) by a post-translational process since the amino acid sequence of $PrP^{Sc}$ is identical to that predicted from cDNA or genomic nucleic acid sequences. Glycosylation patterns are also identical between $PrP^{C}$ and $PrP^{Sc}$. Moreover, Caughey and Raymond (1991) demonstrated that $PrP^{Sc}$ is made from a cell surface precursor that is identical to the normal PrP. $PrP^{Sc}$ differs from the normal, membrane-bound cellular prion protein by its relative protease resistance. Treatment with proteinase K (PK), for instance, results in complete proteolysis of $PrP^{C}$, whereas in $PrP^{Sc}$, the N-terminal part is removed before the amino acid at position 90 (human numeration) (SEQ ID NO:1). The protease-resistant core left is designated PrP27-30 after its electrophoretic behavior in SDS-PAGE as a protein molecule with $M_r$=27-30 kDa, and this molecular species retains full infectivity.

Further distinguishing features of $PrP^{Sc}$ are its thermal stability, a strong tendency to aggregate and insolubility in non-denaturing detergents, apparently connected with a different molecular structure. All attempts to identify a post-translational chemical modification that features in the conversion of $PrP^{C}$ into $PrP^{Sc}$ have been unsuccessful.

The lack of a molecular explanation for the observed differences between $PrP^{Sc}$ and $PrP^{C}$ led to the proposal that they must differ in conformation. Indeed, Fourier transform infrared spectroscopy detected a content of 43% of β-sheet and 30% of α-helix structure for purified hamster $PrP^{Sc}$ and an even higher P-sheet content of 54% for PrP27-30. On the other hand, a low content of β-sheet structure and a high α-helix content of 42% was found in $PrP^{C}$, suggesting differences in secondary structure between the aberrant and normal forms of PrP (Pan et al., 1993).

Due to its better solubility and the availability of recombinant forms of $PrP^{C}$, the three-dimensional structure of mouse PrP (121-231), involving three α-helices and a short antiparallel P-sheet, could be established by NMR (Riek et al. 1996). In the mature murine $PrP^{C}$ (23-231), this segment seems to have the same fold (Riek et al., 1997). Also, the spatial structure of recombinant hamster PrP (29-231) has been examined (Donne et al., 1997).

A species barrier for prion infection has been convincingly documented and found to vary widely depending on the pair of species involved and the direction of transmission. A structural basis for this species barrier is theoretically related to part or all of the amino acid replacements between the PrP of a given pair of species (Billeter et al., 1997).

Within species, genetic polymorphism in the PrP gene has been found, for example, with mice, humans and sheep. In sheep, amino acid substitutions in PrP at a few different positions were found to correlate with different predispositions for the development of scrapie (Laplanche et al., 1993; Hunter et al., 1994; Belt et al., 1995; Bossers et al., 1996).

Studies of scrapie in goats and mice demonstrated reproducible variations in disease phenotype (length of incubation times and pattern of vacuolation) with the passage of prions in genetically inbred hosts (Bruce and Fraser, 1991). The distinct varieties or isolates of prions were called "strains." Safar et al. (1998) made plausible that the biological properties of prion strains are enciphered in the conformation of $PrP^{Sc}$ and that strains represent different conformations of $PrP^{Sc}$ molecules. Infection of Syrian hamsters with eight different hamster-adapted scrapie isolates produced $PrP^{Sc}$ molecular species which, isolated from brains in the terminal stages of disease, differed with respect to protease resistance and unfolding behavior under denaturing conditions. Differences in glycosylation have also been proposed as "strain-specific" properties (Collinge et al., 1996).

Animals and humans lack a TSE disease-specific immune response and TSE diagnosis is based mainly on histopathological examination, which relies on the observation of neuronal degeneration, grey matter vacuolation (the spongiform change) and astrocytosis. A distinguishing feature of TSEs is the accumulation of aberrant protein ($PrP^{Sc}$) in the brain under continuing biosynthesis of the normal cellular $PrP^{C}$. Species differences exist, however, since the relative accumulation of $PrP^{Sc}$ in brains of hamster and mouse is approximately ten times as high as in the ruminant. Unlike the normal $PrP^{C}$, $PrP^{Sc}$ can aggregate into amyloid-like fibrils and plaques and is a major component of brain fractions enriched for scrapie activity. Therefore, a more specific diagnosis of TSEs is detection of $PrP^{Sc}$, either in situ, e.g., by immunohistochemistry, or in tissue homogenates, e.g., by Western blot.

Several poly- or monoclonal antibodies to PrP have been described. The antisera were raised in mice, hamsters, rabbits and PrP null mice and as immunogens, peptides (as linear epitopes), purified and formic acid-treated $PrP^{Sc}$ from mice, hamster or sheep and recombinant PrP are being used. However, except for one case (Korth et al., 1997), there have been no antibodies developed that can discriminate between native forms of $PrP^{C}$ and $PrP^{Sc}$, and such antibodies cannot likely discern the difference between prion strains.

By Western blotting or immunohistochemistry, $PrP^{Sc}$ could be detected in sheep in brain, spleen, tonsil or lymph node material and even in a preclinical stage of scrapie (Schreuder et al., 1998). However, in BSE-infected cattle, $PrP^{Sc}$ could not be detected outside the central nervous system, not even when clinical symptoms were present.

The intriguing mechanism of prion replication is not fully understood. According to the prevailing theory, the infectious $PrP^{Sc}$ acts as a template in the replication of nascent $PrP^{Sc}$ molecules. In other words, $PrP^{Sc}$ imposes its own conformation upon the cellular form $PrP^{C}$ or an intermediate form. A thus far unknown protein X may function as a molecular chaperone in this formation of $PrP^{Sc}$ (Prusiner et al., 1998).

Because of the connection between BSE and the nvCJD, and the possible transfer of BSE to other species including sheep, there is a need to monitor slaughter cattle and sheep for the presence of aberrant prion protein before the meat and meat products enter the human and animal food chain or into pharmaceuticals prepared for human and animal use. Mass screening of sheep and cattle should also be of help in view of eradication programs of scrapie and BSE. Moreover, human blood and blood products may form a health threat on account of possible contamination with blood of CJD patients and the recent occurrence of the nvCJD. For these monitoring purposes, a detection method for aberrant prion protein has to be developed that should be both fast, sensitive, reliable and simple.

Bioassays for $PrP^{Sc}$ in which different doses of the analyte are administered to target animals are generally regarded a gold standard but otherwise are cumbersome and costly. Moreover, their quantitative character is limited by a high variation. Immunohistochemical (IHC) approaches are very useful insofar as the presence of the analyte is directly made visible in the infected tissue. In particular, testing the sample by histology or cytology allows a morphological comparison of healthy and diseased cells or tissue. Also, the presence of $PrP^{Sc}$ can be indicated in a preclinical phase. However, and in general, histological or cytological methods are not quantitative and hardly applicable on a large scale.

For the diagnosis of TSEs founded on the demonstration of $PrP^{Sc}$ in infected tissues and for the assessment of $PrP^{Sc}$ itself, several methods have been described and all are on an immunochemical basis. Most of these tests have been developed and used for research-like purposes, for instance, in order to quantify $PrP^{Sc}$ during purification procedures. In some cases, calibration was with recombinant PrP (hamster or mice) or with $PrP^{Sc}$, purified from scrapie-infected brains. Otherwise, responses were expressed as a function of mg tissue equivalents; in this way, sensitivity could also be assessed by the minimum amount of tissue required for the $PrP^{Sc}$ detection.

ELISA systems were designed for detection of $PrP^{Sc}$, isolated from brains of scrapie-affected mice and hamsters (Kascsak et al., 1987) and $PrP^{Sc}$ from murine brain and spleen (Grathwohl et al., 1997). In these assays, the $PrP^{C}$ fraction was beforehand removed by PK treatment and the purified and solubilized analyte was directly coated onto the microtiter plate. Solubilization of $PrP^{Sc}$ was by treatment with SDS or extraction with 77% formic acid, drying and resuspension in buffer (Kascsak et al. 1987). The denaturing action of formic acid was found to enhance the antibody response to $PrP^{Sc}$ considerably, compared to untreated or SDS-treated material. In this ELISA, rabbit antiserum to the mouse scrapie strain ME7 $PrP^{Sc}$ was used.

Also, successive solubilization of purified $PrP^{Sc}$ by boiling in SDS, precipitation in cold methanol and sonication in 3-4 M guanidine thiocyanate (gdnSCN) (Grathwohl et al., 1997) apparently enhanced coating efficiency and/or epitope density under the denaturing action of gdnSCN. On the other hand, dissolving $PrP^{C}$ in SDS appeared to inhibit adsorption of $PrP^{Sc}$ onto the polystyrene microtiter plate. Although Grathwohl et al. (1997) state that their method could be a basis for a sensitive screening method for $PrP^{Sc}$ in crude tissue extracts, their extraction and purification steps are impracticable and time consuming (over 22 hours). The sensitivity for brain tissue was such that $PrP^{Sc}$ could be detected in 39 mg brain equivalents; the corresponding figure for spleen tissue amounted to 313 mg. Bell et al. (1997) report comparative research of five research centers of in-house immunohistochemical methods for the detection of aberrant protein in CJD by histological staining of brain tissue sections. As to the use of gdnSCN, two of the five centers employ, in addition to formic acid, gdnSCN to pretreat their tissue sections to inactivate the prion agent to allow further processing of the tissues without the danger of infection. However, all over, the value of the addition of gdnSCN is questioned and, in the opinion of one center, it even increases background in histology. Effective decontamination of prion-containing CJD material is also shown in WO 98/32334.

A sandwich type of ELISA was used to monitor the bioproduction of recombinant hamster PrP_(90-231), the protease-resistant core of PrP$^{Sc}$ (Mehlhom et al., 1996). As a capture antibody, the Fab fragment of mAb 3F4 was coated onto the microtiter plate. This antibody was raised against hamster scrapie strain 263K and reacts with hamster, human and feline PrP. As the second antibody, mAb 13A5 (to scrapie hamster PrP$^{Sc}$) was used. Samples from the different stages of purification were measured in this ELISA. However, the practical conditions under which PrP$^{Sc}$, in order to be detected as an antigen, is brought into an unfolded state by chaotropic agents like 3-4 M gdnSCN, are not compatible with the immunochemistry of a sandwich type of ELISA.

Prusiner et al. (1990) used an enzyme-linked immunofiltration assay (ELIFA) that combines the properties of an immuno-dot blot and ELISA technique. By this method, both $PrP^{C}$ and $PrP^{Sc}$ in scrapie brain homogenates of hamsters could be quantified against a standard curve of known amounts of purified hamster PrP27-30 (0.06-4 ng). Brain homogenates, diluted in buffer with 1 M gdnSCN and 0.05% Tween 20, were applied in 5 μl quantities to nitrocellulose membrane in a manifold filtration unit. Sequential steps for immunocomplex formation with mAb 13A5 and conjugation of enzyme were also done on this membrane. For detection, dots were cut out with a puncher and placed into a microtiter plate in which color was developed. Under these conditions, immunoreactivity of the dissociated and (partly) unfolded $PrP^{Sc}$ is indistinguishable from that of $PrP^{C}$ and in this way total PrP was measured. For the determination of the $PrP^{Sc}$ fraction, the homogenate was treated with PK prior to the ELISA and $PrP^{C}$ content was calculated by subtracting the $PrP^{Sc}$ from the total PrP.

Oesch et al. (1994) refined this ELIFA method. Samples were applied on nitrocellulose filters in the ELIFA apparatus, procedures hereafter among which a two-hour-preincubation in 4 M gdnSCN to render the aberrant protein sensitive to protease digestion, and substrate binding to mAb 13A5, up to and including binding with the enzyme, were done on the membrane taken out of the apparatus. For detection, membranes were placed back in the ELIFA apparatus and reacted with substrate solution. Finally, the reaction mixture was pulled through into an ELISA plate placed underneath and color development was measured. This whole procedure took over 20 hours.

Immuno-dot blotting was used by Serban et al. (1990) for the post-mortem diagnosis of Creutzfeldt-Jakob disease in humans, scrapie in sheep and scrapie-infected hamsters and mice. Direct spotting of a rather impure analyte on, e.g., nitrocellulose filters instead of adsorption of a purified fraction of it onto the plastic surface of microtiter wells produces a more robust ELISA variant. This qualitative test was based on the intensified immunoreactivity of $PrP^{Sc}$-containing amyloid plaques after treatment with 3 M gdnSCN and the protease resistance of the $PrP^{Sc}$ isoform.

Brains were extracted in detergent-containing lysis buffer and 4 μl amounts were spotted onto nitrocellulose membranes. Immunoreactivity of the spotted material after successive treatment with PK and 3 M gdnSCN was conclusive for the presence of $PrP^{Sc}$ and confirmation of CJD and scrapie. Rabbit Ab R075 (to purified hamster PrP27-30) was able to detect PrP in the above four species. Out of a total of 28 human brain samples, nine cases found positive by this method were also either defined as CJD or GSS by both clinical diagnosis and a histopathological examination. For two cases found positive by the blot procedure, histopathologic results were not available. The negative results of histopathology for CJD or GSS on the remaining 17 cases coincided also with no indication for $PrP^{Sc}$ with the immuno-dot blot assay. In 12 histologically confirmed cases of natural scrapie in sheep, $PrP^{Sc}$ was detected with the immunoblotting technique in the brains of 11 sheep. There are variations in the distribution of $PrP_{SC}$ in the brain of scrapie-affected sheep, since $PrP^{Sc}$ was found in the spinal cord, cerebellum and pons/medulla of two sheep, but one sheep also had $PrP^{Sc}$ in the frontal and occipital cortex and the thalamus. This means that sampling of brain tissue could lead to false negatives due to regional variations in $PrP^{Sc}$ content. The detection limit of this method for brain extracts of scrapie-infected hamsters and mice ranged from 5-132 mg tissue equivalents, because these amounts still gave clearly visible spots. The duration of the test was, apart from an overnight incubation step, six hours.

Safar et al. (1998) developed a conformation-dependant fluorescent-ELISA that can discern various prion strains of hamsters. The assay detects a region of $PrP^{Sc}$ that, while exposed in normal $PrP^{C}$, becomes folded in the $PrP^{Sc}$ molecule. Eu-labeled mAb 3F4 that reacts with a region of $PrP^{Sc}$ only after unfolding in 4 M gdnHCl and heating at 80° C. for five minutes, was used in this assay. The immunoreactivity of the antibody to the denaturated region, as reflected by the fluorescence signal, is much higher than it is to $PrP^{Sc}$ in its native form. The authors developed an algorithm that takes into account that the immunoreactivity of antibody to denatured PrP in a sample of an affected brain is the summation of enhanced immunoreactivities of $PrP^{Sc}$ and $PrP^{C}$ during the transition from the native to the denatured states. Knowledge of the enhancement of immunoreactivity for $PrP^{C}$ during denaturation was a prerequisite for this approach. For this purpose, calibration curves with different concentrations of purified $PrP^{C}$ were constructed. It appeared that also $PrP^{C}$ showed an enhanced immunoreactivity in 4 M gdnHCl, compared to its native state, albeit in a moderate way (≦1.8×). From the algorithm and the measurements of a native as well as a denatured sample, the content of $PrP^{Sc}$ could be calculated. Although this method was validated for the determination of hamster brain, the authors aim at using it also for the detection of other mammalian prions, including human. In order to improve the detection threshold of the assay, they introduced an initial step to selectively precipitate $PrP^{Sc}$ from raw material with sodium phosphotungstate. In combination with this sample pretreatment, the final sensitivity of the assay could be made high. The sensitivity limit is less than or equal to 1 ng/ml (100 pg) of $PrP^{Sc}$. The test, however, is still far from lending itself to large-scale use in view of too much labor and long incubation times.

Capillary electrophoresis was adapted by Schmerr et al. (1995, 1996, 1998a), as a diagnostic, immunochemical assay for scrapie. The authors claim a high sensitivity (approximately 135 pg $PrP^{Sc}$) of their test by measuring laser-induced fluorescence of a PrP-derived fluorescein-labeled peptide after its separation by free-zone capillary electrophoresis. In a preceding competition step, this peptide was displaced from a preformed complex of the peptide and an antibody directed to the unlabeled peptide in competition with the analyte ($PrP^{Sc}$). Beforehand, $PrP^{C}$ had been removed from the analyte solution by PK treatment. The concentration of rabbit antiserum for complex-preformation was chosen so that the antibody would be limiting in the assay (adjustment to 50% of the maximum amount of immunocomplex). Four anti-(prion)-peptide antisera were prepared and evaluated. Assays using antisera to the peptides spanning mouse amino acid position 142-154 (SEQ ID NO:4) and 155-178 (SEQ ID NO:4) differentiated scrapie-positive sheep from normal animals. In spite of the high sensitivity of this method, sample processing is time consuming (approximately 24 hours) and cumbersome since PrP$^{Sc}$ from brain stem has to be concentrated and purified through steps like ultracentrifugation and HPLC.

Western blotting (WB), in combination with SDS-PAGE, is also a suitable technique for diagnosis of TSEs and a variety of different extraction procedures and Western blotting methods has been described (Race et al., 1992; Beekes et al., 1995).

Usually, PrP$^C$ is extracted from tissues with detergents that solubilize this membrane-bound protein in a mixed micelle. However, PrP$^{Sc}$ in the presence of detergents, aggregates and, therefore, is not solubilized but can be spun down by ultracentrifugation. PrP$^{Sc}$ aggregates dissociate in monomers under the denaturing conditions of heating in SDS solution with β-mercaptoethanol. In this way, PrP$^{Sc}$ is electrophoretically (SDS-PAGE) indistinguishable from PrP$^C$, unless a preceding treatment with PK has been applied. This proteolytic treatment removes PrP$^C$ and leaves PrP27-30, the truncated form of PrP$^{Sc}$.

Race et al. (1992) could find PrP$^{Sc}$ in every brain of eight sheep that were histologically positive for scrapie and even in brains of clinically positive sheep that were not diagnosed as scrapie-positive by histology. For detection, antipeptide antibodies to residues 89-103 (SEQ ID NO:4) and 218-232 (SEQ ID NO:4) of the mouse PrP sequence were used. Apparently, the amount of tissue required to visualize PrP$^{Sc}$ varied among sheep from <2 to 200 mg equivalents of brain tissue. Also, PrP$^{Sc}$ was found in spleens and lymph nodes in seven of eight sheep that had the protease-resistant form detected in brain homogenates.

One method based on WB was officially approved by the European Union (EU) and the World Organization for Animal Health (OIE) for BSE and scrapie diagnosis (Bradley et al., 1994). A minimum amount of 2 mg equivalent of infected scrapie brain allows detection of the PrP27-30.

Above-identified assays have never been used in large screening efforts for the detection of aberrant prion protein, neither in animals nor in humans.

Thus far, two commercial assays have been announced. In 1997, the Swiss company Prionics Inc. launched its "BSE Western Test" intended for mass screening of slaughter cattle. A modified and optimized Western blot method was used to detect the proteinase K-resistant PrP27-30 in bovine brain stem. For immunodetection, mAb 6H4 was used, developed by immunizing PrP-null mice with recombinant bovine PrP. This antibody recognizes residues 147-155 (SEQ ID NO:5) of the bovine sequence as a linear epitope in native PrP$^C$ and denatured PrP$^{Sc}$; this sequence is also recognized in sheep, human, pig and mouse. Incubation with anti-mouse IgG coupled to alkaline phosphatase and detection of the enzymatic product by chemiluminescence were the final steps of the assay. This test requires an incubation step with PK and detects PrP27-30. Reliability is strengthened by the Western blot documentation of the decrease in size (internal control) of the prion protein from 30-33 to 27-30 kDa. The test can be done within hours, and the expectation is that subclinical BSE in post-mortem brains may be detected.

Also, in 1997 the Irish Company Enfer Scientific Ltd. announced the development of a BSE post-mortem test. This immunoassay intended for mass screening uses a PrP antipeptide antiserum to detect PrP27-30 in samples of brain tissue of cattle after removal of PrP$^C$ by PK treatment. Immunodetection was enhanced by chemiluminescence. Their claims are a result within four hours after receipt of samples and a capacity of 14,000 cattle a day and, moreover, the catching of asymptomatic animals.

However, these two commercial tests, although claiming high sensitivity in detecting the aberrant protein, and thus claiming to have a low number of false-negative results, suffer from the low specificity associated with the claimed high sensitivity. When using the above tests, one, therefore, runs an increased risk of falsely identifying a negative sample as false positive, thereby falsely identifying an animal as positive. For example, Switzerland slaughtered herds in which one or more cases of BSE had been confirmed. The "Swiss reference laboratory for animal TSE" examined the brains of these 1761 apparently healthy cattle by an immunohistochemical method for signs of BSE and six positive cases were detected. Also. Prionics Inc. tested these 1761 cattle brains by their "BSE Western Test." Four positive outcomes were identical to the ones found by the reference laboratory, the other two were indicated as negative and, moreover, two other cattle were found positive by Western blotting. Thus, a total of eight positive reactors were found, four of which overlapped. These eight were re-examined in the laboratory of Dr Kretzschmar (University of Gottingen) and in addition to the four undisputed cases, one of the two questionable cases identified by the reference laboratory could be confirmed (info: New Scientist, 1998, July 4 and Internet). Prionics, for example, scored 0.1% false positives, indicating that in one of every thousand cases, a sample causes a false alarm due to false positivity.

Tests scoring false-positive results (being, in general, not specific enough) have other consequences than tests scoring false-negative results (being, in general, not sensitive enough).

"False negative" means that, in essence, a positive sample from a positive individual is scored negative and, thus, is not suspected of having a TSE, while in truth, the individual does have a TSE. A false-negative diagnosis thus results in missing positive cases.

For humans, "false negative" means that no diagnosis of TSE is made where the human actually has a TSE. This causes a wrong prognosis being established and wrong treatment being given, until a second test is done.

For animals, especially in those cases where slaughtered animals are tested, "false negative" means that no diagnosis of TSE is made where the animal was actually infected and possibly capable of spreading the disease without having been noticed. Meat and other products from such a false-negative animal may contain aberrant prion protein. Such meat and meat products will be traded and eaten and can thus be a source for further infection, notably of humans who even falsely trust that the animal has been tested well and the meat or meat product bears no risk.

"False positive" means that, in essence, a negative sample from a negative individual is scored positive, and thus is at least suspected of having a TSE, while in truth, the individual does not have a TSE at all, but possibly another condition.

For humans, "false positive" means that a false diagnosis of TSE is made, here again resulting in false prognosis and in faulty treatment. If the individual is not treated well as a consequence of the misdiagnosis, his or her possible other disease condition (the symptoms of which, for example, gave rise to the decision to test for TSE) receives no proper treatment.

For animals, "false positive" means that a false diagnosis of TSE is made, however, since TSEs are notifiable diseases that in general are met with strict eradication measures, the animal shall, at least in most Western countries, be killed and destroyed. Furthermore, the herd from which the animal originated runs the same risk of being destroyed when the diagnosis is not corrected. For the slaughterhouse, it might mean that special laborious decontamination actions have to be implemented, which mean temporary interference of use of the facilities and thus considerable loss of productivity. Additionally, the country where the animal or herd is falsely diagnosed for having a case of TSE among its animals will be met with export restrictions. It goes without saying that, especially when the country has no (present) reported cases of TSE, such a false-positive diagnosis is highly detrimental for the country's position on foreign markets for animal products.

Understanding the above risks associated with false-negative or false-positive diagnoses becomes even more complicated when one understands that, in general, the level of false positives scored by a diagnostic method or test is inversely related to the number of false negatives scored by the same test. It is an old diagnostic truth that, in many instances, a very sensitive test (having low numbers of false negatives) cannot be very specific (and, thus, has a relative high number of false positives) and vice versa. However, and especially for mass screening tests that do not comprise histology or cytology, and wherein many samples need to be tested, tests having both high sensitivity and specificity are desired.

DISCLOSURE OF THE INVENTION

Provided is the use of guanidine thiocyanate (gdnSCN) or a functional equivalent thereof for treating at least one sample derived from a mammal for reducing the risk of scoring a false-positive test result in testing the sample for the presence or absence of aberrant prion protein, in particular, in testing the sample in a method other than histology or cytology. Using guanidine thiocyanate or its functional equivalents allows reduction of the signal arising from the normal prion protein ($PrP^C$) so that, for example, when a gdnSCN-treated sample is compared with an untreated sample, the $PrP^C$ signal is greatly reduced. See, for example, FIG. 3 herein describing the reduction of the signal from a $PrP^{Sc}$-negative sample obtained by a use according to the invention.

Also provided is the use of guanidine thiocyanate (gdnSCN) or a functional equivalent thereof for treating at least one sample derived from a mammal for reducing the risks of scoring both a false-positive test result or a false-negative test result in non-histologically or non-cytologically testing samples for the presence or absence of aberrant prion protein.

Further provided is the use of the invention in an immunoassay. The invention provides a reliable, simple and fast method, comprising use of gdnSCN or a functional equivalent thereof in a method for diagnosis of TSE being both highly specific as well as highly sensitive.

Also provided is a method for reducing the risk of scoring a false-positive test result in testing a sample derived from a mammal for the presence or absence of aberrant prion protein comprising treating at least one sample with gdnSCN or a functional equivalent thereof. Because of its simplicity and, due to its non-histological nature, speed, a method according to the invention particularly lends itself to mass screening purposes of, e.g., post-mortem tissues in the slaughter-line of ruminants such as cattle and sheep, but it is equally suitable in testing samples derived from other ruminants or experimental animals. In the human field, the method could be used for, e.g., screening lymphoid tissues and blood-derived products. Essentially, samples from all tissues, body fluids (e.g., blood, liquor) and feces can be used.

BSE or subclinical (silent) cases of BSE can, for example, be detected in samples automatically taken from the brain at the time that the heads are cut off from the slaughter-animals' trunk. The method can also be used in preclinical stages during the development of scrapie since tonsils that can be taken from the living animal are proven to be an indicator tissue for preclinical scrapie and to contain $PrP^{Sc}$ (Schreuder et al., 1998).

With scrapie in sheep as a model, we developed a method to unambiguously distinguish $PrP^{Sc}$ from $PrP^C$. This can be done on the basis of immunodetection of $PrP^{Sc}$ without the need of a preceding elimination of $PrP^C$ by enzymatic proteolysis (FIG. 3).

In modified embodiments, provided is a use comprising the use of a protease for treating the sample to reduce the presence of normal prion protein (FIG. 4). This design is, for example, suited for the detection of aberrant prion protein in BSE.

Immunologically, the signal of $PrP^{Sc}$ can be enhanced in the presence of chaotropic agents. This enhancement is undoubtedly effected by dissociation of the polymeric $PrP^{Sc}$ into oligo- or monomeric units, resulting in an increase of the number of epitopes available for the antibody. Moreover, the epitopes may be better exposed to the antibody through the protein defolding action of the denaturant.

Furthermore, provided are methods further comprising treating at least one first sample with gdnSCN or a functional equivalent thereof and leaving at least one second sample untreated with gdnSCN or a functional equivalent thereof and comparing the test result of the first sample with the second sample. We can, for example, discriminate between TSE-positive and -negative cases after duplicate dot blotting of extracts of brain tissue onto a membrane. Extraction is in detergent-containing (lysis) buffer. One aliquot is left untreated and the other one is treated in 4 M gdnSCN (FIG. 3) or, after PK digestion, treated in 4 M gdnSCN (FIG. 4). Then, after immunostaining, the treated sample is compared to the untreated sample. The signal of the normal protein ($PrP^C$) is greatly reduced or retains the same intensity upon treatment and can be further reduced by protease K digestion. In this way, comparison of untreated and treated samples leads to a decrease or no increased of signal in samples from normal individuals, but to a significant increase of signal in samples from TSE-affected animals. By this dual internal control, the discriminating value of the test is considerably reinforced.

Also provided is a method comprising immunological detection of the aberrant prion protein using at least one antibody directed against the aberrant protein, preferably directed against a proteinase K-resistant part of the aberrant prion protein, for example, wherein the antibody is directed against a proteinase K-resistant N-terminal part of the aberrant prion protein. Monoclonal or polyclonal antibodies can be used, possibly the antibody is raised against a peptide derived from the prion protein, for example, wherein the peptide is selected from an N-terminal group consisting of residues 94-111 (like 94-105 (SEQ ID NOS:7-11) and 100-111 (SEQ ID NOS:12-15)), a C-terminal group consisting of residues 223-234 (SEQ ID NOS:27-30) and a group consisting of residues 145-177 (SEQ ID NOS:21-26) (sheep numbering) or sequential homologues of the PK-resistant part of $PrP^{Sc}$ (FIG. 2) or functional equivalents thereof.

Also provided is a method according to the invention wherein the protein is immunologically detected in an enzyme-linked immunoassay, for example, wherein the enzyme-linked immunoassay comprises a dot blot assay.

Also, provided is a test kit having been provided with means for performing a method according to the invention. This kit, for example, contains a carrier matrix for spotting sample extracts from tissues, organs, cells or body fluids (e.g., nerve tissue, blood cells, etc.), buffers, solutions of gdnSCN and PK, primary antibody, enzyme-labeled second antibody and enzyme-substrate. In a most preferred embodiment, the method or test kit is designed for mass-screening purposes.

The invention is further described in the detailed description herein without limiting the invention.

BRIEF DESCRIPTION OF THE DRAWINGS

FIG. 1: Amino acid sequences of human (SEQ ID NO:1), rabbit (SEQ ID NO:2), hamster (SEQ ID NO:3), mouse (SEQ ID NO:4), cattle (SEQ ID NO:5) and sheep (SEQ ID NO:6) PrP genes. The entire amino acid sequence of human PrP is given (SEQ ID NO:1); open spaces in the other sequences indicate identity (SEQ ID NOS:2-6). Polymorphisms are indicated in bold at the top of each block and relate to the shaded positions. ↓: PHGGGWGQ. |: protease-sensitive site, right of which the sequence for the PK-resistant core of PrP$^{Sc}$ is found. The mature PrP is devoid of N- and C-terminal signal peptides (in huPrP (SEQ ID NO:1): amino acids 1-22 and 232-253, respectively). human (SEQ ID NO:1): H. A. Kretzschmar, S. B. Prusiner, L. E. Stowring and S. J. DeArmond (1986), "scrapie prion proteins are synthesized in neurons," *Am. J. Pathol.* 122:1-5; rabbit (SEQ ID NO:2): Loftus B. and M. Rogers (1997), "characterization of a prion protein (PrP) gene from rabbit: a species with apparent resistance to infection by prions," *Gene* 184:215-219; R. Rubenstein, R. J. Kascsak, M. Papini, R. Kascsak, R. I. Carp, G. LaFauci, R. Meloen and J. Langeveld (1998), *J. Neuroimmunology* (accepted); golden Syrian hamster (SEQ ID NO:3): K. Basler, B. Oesch, M. Scott, D. Westaway, M. Walchli, D. F. Groth, M. P. McKinley, S. B. Prusiner and C. Weissmann (1986), "scrapie and cellular PrP isoforms are encoded by the same chromosomal gene," *Cell* 46:417-428; mouse (SEQ ID NO:4): C. Locht, B. Chesebro, R. Race and J. M. Keith (1986), "molecular cloning and complete sequence of prion protein cDNA from mouse brain infected with the scrapie agent," *Proc. Nat'l. Acad. Sci. USA* 83:6372-6376; D. Westaway, P. A. Goodman, C. A. Mirenda, M. P. McKinly, G. A. Carlson and S. B. Prusiner (1987), "distinct prion proteins in short and long scrapie incubation period mice," *Cell* 51:651-662; cattle (SEQ ID NO:5): W. Goldmann, N. Hunter, T. Martin, M. Dawson and J. Hope (1991), "different forms of the bovine PrP gene have five or six copies of a short, g-c-rich element within the protein-coding exon," *J. Gen. Virol.* 72:201-204; sheep (SEQ ID NO:6): W. Goldmann, N. Hunter, J. D. Foster, J. M. Salbaum, K. Beyreuther and J. Hope (1990), "two alleles of a neural protein gene linked to scrapie in sheep," *Proc. Nat'l. Acad. Sci. USA* 87:2476-2480.

FIG. 2: Peptide sequences derived from the prion protein structures of six species (hu=human (SEQ ID NOS:7, 12, 16, 21, 27), rb=rabbit (SEQ ID NOS:8, 13, 17, 22, 28), ha=hamster (SEQ ID NOS:9, 14, 18, 23, 29), mo=mouse (SEQ ID NOS:9, 14, 19, 24, 29), bo=cattle (SEQ ID NOS:10, 15, 20, 25, 30), ov=sheep (SEQ ID NOS:11, 12, 20, 26, 30)). The amino acid sequence of the human peptides is given (SEQ ID NOS:7, 12, 16, 21, 27); open spaces in the other sequences indicate identity (SEQ ID NOS:8-11, 13-15, 17-20, 22-26, 28-30). Antipeptide antibodies were raised in rabbits against the peptides of the ovine structure. Corresponding antisera are indicated R5xx at the top of each set of sequences. The set of sequences under the heading R521, R522 (to ovine sequence 94-105) includes the amino acid sequences of hu=human (SEQ ID NO:7), rb=rabbit (SEQ ID NO:8), ha=hamster (SEQ ID NO:9), mo=mouse (identical to hamster) (SEQ ID NO:9), bo=cattle (SEQ ID NO:10), and ov=sheep (SEQ ID NO:11). The set of sequences under the heading R504, R505, R593-596 (100-111) includes the amino acid sequences of hu=human (SEQ ID NO:12), rb=rabbit (SEQ ID NO:13), ha=hamster (SEQ ID NO:14), mo=mouse (identical to hamster) (SEQ ID NO:14), bo=cattle (SEQ ID NO:15), and ov=sheep (identical to human) (SEQ ID NO:12). The set of sequences under the heading R568 (126-143) includes the amino acid sequences of hu=human (SEQ ID NO:16), rb=rabbit (SEQ ID NO:17), ha=hamster (SEQ ID NO:18), mo=mouse (SEQ ID NO:19), bo=cattle (SEQ ID NO:20), and ov=sheep (identical to cattle) (SEQ ID NO:20). The set of sequences under the heading R532 (145-177) includes the amino acid sequences of hu=human (SEQ ID NO:21), rb=rabbit (SEQ ID NO:22), ha=hamster (SEQ ID NO:23), mo=mouse (SEQ ID NO:24), bo=cattle (SEQ ID NO:25), and ov=sheep (SEQ ID NO:26). The set of sequences under the heading R523, R524 (223-234) includes the amino acid sequences of hu=human (SEQ ID NO:27), rb=rabbit (SEQ ID NO:28), ha=hamster (SEQ ID NO:29), mo=mouse (identical to hamster) (SEQ ID NO:29), bo=cattle (SEQ ID NO:30), and ov=sheep (identical to cattle) (SEQ ID NO:30).

DETAILED DESCRIPTION OF THE INVENTION

Materials and Methods

Figure 3:
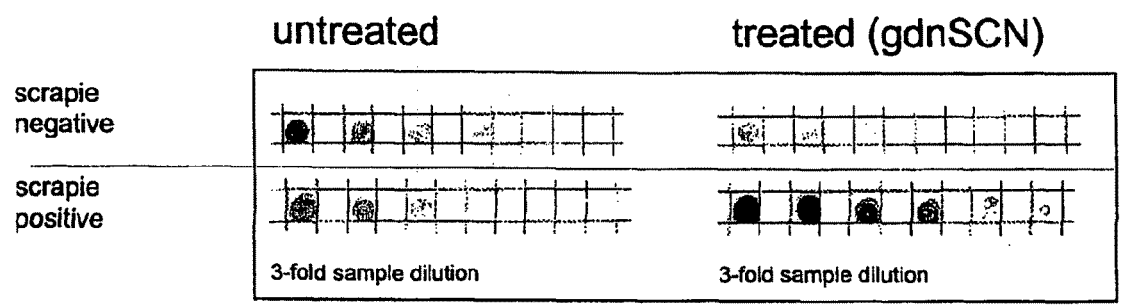
FIG. 3: Prion test in which the extract was applied to two pieces of NC membrane indicated: untreated and treated. A 10% (wt/vol. %) extract of brain-stem tissue was ⅓ diluted and 1 μl applied to NC-membrane. Then, one piece of membrane was incubated in solution without gdnSCN (untreated) and the other was incubated in 4 M gdnSCN-containing solution (treated). Further incubations for immunochemical visualization with first antibody (R522-7) and alkaline-phosphatase conjugate were according to standard procedures. In each three-fold dilution series, the first (left) spot represents 33 μg of tissue equivalents.
Figure 4:
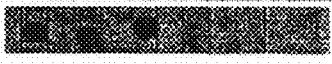
FIG. 4: Prion test in which the extract was applied to two pieces of PVDF membrane indicated: untreated and treated. For each negative and positive case, a 10% (wt/vol. %) extract of brain-stem tissue was prepared and divided in two portions, of which one was incubated with proteinase K (PK-digested extract) or not (undigested extract). Next, each of the extracts was ⅓ diluted and 3 μl applied to PVDF membrane. Then, the piece of membrane with the undigested extract was incubated in solution without gdnSCN (untreated) and the membrane with digested extract was incubated in 4 M gdnSCN-containing solution (treated). Further incubations for immunochemical visualization with first antibody (R595-4) and alkaline-phosphatase conjugate were according to standard procedures. In each three-fold dilution series, the first (left) spot represents 100 μg of tissue equivalents.

Phosphate buffered saline (PBS), pH 7.2 contained 136.89 mM NaCl, 2.68 mM KCl, 8.10 mM $Na_2HPO_4$ and 2.79 mM $KH_2PO_4$ in water.

PBTS: 0.2% (w/v) Tween-20 in PBS.

Two extraction buffers were used:
(a) 10 mM phosphate buffer, pH 7.0, 0.15 M NaCl and 0.25 M sucrose, used by Pan et al. (1992) to prepare microsomal fractions;
(b) lysis buffer (Collinge et al., 1996) consisted of 0.5% (w/v) Tergitol (type NP-40, nonylphenoxy polyethoxy ethanol, Sigma NP-40) and 0.5% (w/v) deoxycholic acid, Na-salt (Merck) in PBS, pH 7.2.

Guanidine thiocyanate (gdnSCN, purity >99%; Sigma G 9277) solutions of 4 M were made up in water (pH 5.8).

Alkaline phosphatase-conjugated goat anti-rabbit IgG (GAR/AP) was from Southern Biotechnology As. (ITK, Diagnostics B.V., Uithoorn).

Substrate for alkaline phosphatase was 5-bromo-4-chloro-3-indolyl phosphate/nitro blue tetrazolium (BCIP/NBT; tablets; Sigma B5655).

Usually, after PrP extraction, protease inhibitors were added to the extracts. (Complete, protease inhibitor cocktail tablets; Boehringer Nr. 1697498, Mannheim, Germany.)

Proteinase K (EC 3.4.21.14, 20 units/mg lyophilisate Nr. 745723) and Pefabloc SC (4-(2-aminoethyl)-benzenesulfonyl fluoride, hydrochloride Nr. 1585916) were also from Boehringer. Incubation conditions for PrP extracts with PK were 50 μg/ml enzyme for 30 minutes at 37° C. In order to stop this enzymatic reaction, the incubation mixture was made 1 mM in Pefabloc added from a 100 mM stock solution of the inhibitor in water.

As a blocking agent, nonfat dry milk (Protifar, Nutricia) was used.

A number of hydrophilic (14) and hydrophobic (5) membranes were tested as carrier matrix. The most successful representatives, polysulphone or nitrocellulose membrane types, were selected. Three membrane types were routinely used: nitrocellulose (NC) membrane with a 3 mm screen (Protran BA 85/21; 0.45 mm Nr. 405891) was from Schleicher and Schuell GmbH (Dassel, Germany), Immobilon-P (polyvinylidenedifluoride, PVDF) from Millipore B.V. (Etten Leur) and Zeta-Probe (quaternary amine-nylon membrane) was from BioRad.

An Ultra-Turrax T25 mixer with a 10 mm shaft (IkA Labortechnik Gmbh, Staufen, Germany) was used to homogenize brain tissue. The shaft was decontaminated in 1 M NaOH.

Water of "Milli-Q" (Millipore) quality was used throughout.

Primary Antibodies

These were intentionally designed for scrapie diagnosis. Antisera were induced in rabbits using synthetic peptides with sequences based on the sequence of ovine PrP protein. The sequences have such differences with the rabbit PrP sequence that they induce not only antibodies that recognize these peptides but also the authentic PrP protein. Other animal species like mouse, which have sequence differences, could be suitable as well. The sequences used for immunization were selected from the protease K-resistant domain of $PrP^{Sc}$. The selected 12-mer sequences (SEQ ID NOS:11, 12, 30) represent domains that have a low tendency to form secondary structure (α-helix or β-sheet). The antisera are reactive in diagnostic dot blotting but also in Western blotting of both $PrP^{C}$ and $PrP^{Sc}$, in ELISAs with, as coated antigens, the above peptides or PrP protein, and in immunohistochemical detection. With the peptide derived from the ovine prion protein sequence 94-105 (SEQ ID NO:11), antisera R521 and R522 were produced in rabbits. Likewise, sequence 100-111 (SEQ ID NO:12) yielded antisera R504, R505, R593, R594, R595, and R596, and sequence 145-177 (SEQ ID NO:26) antiserum R532. The sequence 126-143 (ovine and bovine) (SEQ ID NO:20) gave rise to antiserum R568, while sequence 223-234 (ovine and bovine) (SEQ ID NO:30) yielded antisera R523 and R524. Peptides were synthesized and used to raise antipeptide antisera in rabbits following previously published procedures (Van Keulen et al., 1995). Antisera were confirmed to be specific for sheep PrP (both undigested and after proteinase K treatment) on Western blots of partially purified prion protein from scrapie-affected sheep brain.

Sheep samples (brain stem, cervical spinal cord) were from scrapie-affected sheep, diagnosed by histopathological and immunohistochemical examination of the brain and from normal healthy sheep (Van Keulen et al., 1995). Samples from BSE-diagnosed cattle (histopathology, immunohistochemical examination and Western blotting) were from the cervical spinal cord or brain stem.

Procedure for immuno-dot blotting: 0.5 g portions of brain tissue were cut down with a scalpel and homogenized with an Ultra-Turrax mixer (20,000 rpm/15 seconds) in 4.5 ml of ice-cold lysis buffer. The homogenates were centrifuged at 1000×g for ten minutes or used without centrifugation as crude homogenate. If appropriate, an aliquot of the homogenate was incubated with PK at 37° C. for 30 minutes, after which the reaction was stopped with Pefabloc (1 mM). Otherwise, a cocktail of protease inhibitors was immediately added to the homogenate. Suitable dilutions of the turbid supernatants or crude homogenates in lysis buffer were spotted in 1-3 μl amounts onto two blotting membranes and left for 15 minutes. One membrane was incubated in 4 M gdnSCN for ten minutes and the other membrane was left untreated. Washing of the treated membranes was for ten minutes in PBS on a rocking platform.

Membranes were blocked with 5% (w/v) Protifar in PBS for one hour at 20° C. and washed in PBTS with 1% (w/v) Protifar for five minutes at 20° C. A one to two-hour incubation with the primary antibody (1/1000 diluted in PBTS) at 20° C. was followed by three washing steps in PBTS for five minutes each. Next, the membranes were incubated with AP-conjugated goat anti-rabbit IgG (1/1000 diluted in PBTS) for one to two hours at 20° C. and washed in PBTS three times for five minutes. Substrate solution was added and the reaction was stopped with water.

Results

Detection of Aberrant Prion Protein in Scrapie

Extraction efficiency for $PrP^{Sc}$

After homogenizing brain stem tissue of a scrapie-affected sheep in extraction buffer (a) or in (b) (=lysis buffer) and low-speed centrifugation that yielded supernatant 1, aliquots of this supernatant were again centrifuged at a higher speed (11,000×g, ten minutes: "high speed" supernatant 1). The loose pellets left from the first centrifugation step were adjusted with buffer to the original volume, re-extracted and centrifuged at 1000×g, which yielded a supernatant 2 and a loose pellet. In addition, aliquots of all fractions were treated with PK.

One μl extracts (diluted 1, 1/10 and 1/100× in their respective buffers) were spotted onto NC and immunodetection was with R522-7, an antiserum that has proven to detect ovine PrP (Van Keulen et al., 1995).

For lysis buffer, the highest signal intensity was obtained for the supernatant 1. Compared to the results for lysis buffer, the signals for extraction buffer (a) were lower for all fractions, except for the pellet. For fractions of the lysis buffer, decreased intensities were observed after pretreatment with proteinase K, especially for supernatant 2, which indicates that this fraction is relatively enriched with $PrP^{C}$.

We observed dramatically intensified signals for the lysis buffer extracts when these were diluted in 4 M gdnSCN. For supernatant 1, even after a 100-fold dilution, the signal was clearly visible, which means that in these scrapie brain stems, PrP can be made visible in a tissue equivalent of 1 μg.

Divergent Signal Enhancement for $PrP^{Sc}$ and $PrP^{C}$

Investigation of brain stem extracts of a scrapie-negative sheep in lysis buffer revealed, even in an eighty-fold dilution, clear signals of $PrP^{C}$. However, after pretreatment with PK, a signal could no longer be observed. Surprisingly, instead of applying this PK treatment, dilution of tissue extract in 4 M gdnSCN also led to a dramatic decrease of signal intensity for $PrP^C$.

Next, instead of diluting lysis buffer-extracted samples in 4 M gdnSCN, we applied serial dilutions of brain extracts of scrapie-positive and -negative sheep in duplicate on NC membranes and incubated one membrane in 4 M gdnSCN for ten minutes while the other one was left untreated.

Immunodetection revealed that we could easily discriminate between scrapie-positive ($PrP^{Sc}$ and $PrP^C$) and scrapie-negative ($PrP^C$) samples: a higher intensity with 4 M gdnSCN compared to an untreated sample means scrapie positive, while a lower intensity with gdnSCN means scrapie negative.

This finding is the basis for a rapid and simple diagnostic test for TSEs. In this test, there is, in general, no need for a preceding removal of $PrP^C$ from the negative sample.

Alternative Denaturants and Antisera

As an alternative for gdnSCN, we investigated the effects of other chaotropic agents. After dot blotting, 3 μl dilutions of extracts of scrapie-positive and -negative brain stems, separate NC membranes were incubated for ten minutes in chaotropic agents. The solutions used were: 4 M gdnSCN, 7.2 M urea, 4 M KSCN, 1 M thiourea, NaOH (pH 11) in water and 98% formic acid; besides one membrane was left untreated as a blank. Results for immunodetection after KSCN and thiourea did not differ from the blank. Urea induced a slight increase for the scrapie-positive material and formic acid enhanced the intensity to the level of gdnSCN, although this acid caused considerable shrinking of the NC membrane. Optimum enhancement with PVDF as a carrier was achieved by using 50% formic acid; no membrane shrinkage was then observed. NaOH (pH 11), on the other hand, increased the signal for scrapie-negative material.

Treatment with 4 M gdnSCN turned out to be the best discrimination between scrapie-positive and -negative tissue samples. Moreover, this effect appeared to be pH-invariant since solutions of 4 M gdnSCN at pH 4 and 7 (in 50 mM phosphate buffer), pH 6 (in water) and pH 9 (in 50 mM carbonate buffer) gave identical results.

Five classes of antipeptide antisera to linear epitopes of sheep PrP sequences (94-105 (SEQ ID NO:11), 100-111 (SEQ ID NO:12), 126-143 (SEQ ID NO:20), 145-177 (SEQ ID NO:26) and 223-234 (SEQ ID NO:30)) were examined. For comparative reasons, all sera were used in a 1/500 dilution in PBTS. Antisera to the 94-105 sequence (SEQ ID NO:11) (R521, R522) and to the 100-111 sequence (SEQ ID NO:12) (R505) proved to have the best differentiating power. On the other hand, with the antisera R568 and R532 to the sequences 126-143 (SEQ ID NO:20) and 145-177 (SEQ ID NO:26), respectively, no immuno-enhancing effect of 4 M gdnSCN on $PrP^{Sc}$ could be detected.

Blotting Membranes

Comparison of results on NC membrane with those on Zeta-Probe showed, for the latter, a strong aspecific coloring of the entire membrane and consequently quaternary amine-nylon as a carrier was unsuitable. On the other hand, compared to nitrocellulose, a stronger adsorption for PrP was shown for the PVDF membrane (Immobilon-P).

Detection of Aberrant Prion Protein in BSE

From brains of BSE-positive cattle, obtained from The Netherlands, the UK, Ireland, Belgium and Switzerland, and of Dutch BSE-negative cattle (diagnosed by histopathology and immunohistochemical examination), brain stems were extracted with lysis buffer in the same manner as for sheep, and the low-speed supernatant 1 was used for further examination. Brain stem extracts from confirmed scrapie-negative and -positive sheep were used for comparison. Aliquots of extracts were also treated with proteinase K and 3 μl amounts of dilutions in lysis buffer of PK-treated and untreated extracts were spotted onto NC membranes. Immunodetection was with 1/1000 dilutions of antisera to the 12-mer sequences 94-105 (SEQ ID NO:11) (antiserum R521), 100-111 (SEQ ID NO:12) (R505, R595, R596), 223-234 (SEQ ID NO:30) (R523, R524) and to the longer sequences 126-143 (SEQ ID NO:20) (R568) and 145-177 (SEQ ID NO:26) (R532).

Highest immunoreactivity was shown with antisera R505 and R595. After incubation with 4 M gdnSCN, signal intensity of BSE-negative samples diminished; however, the immuno-enhancing effect of 4 M gdnSCN on $PrP^{Sc}$ in BSE-positive samples did not reach a comparable high level as for sheep $PrP^{Sc}$ in scrapie. Surprisingly, antisera R523, R524 and especially R532 showed stronger immunoreactivity with bovine $PrP^{Sc}$ than with $PrP^C$. Immunoreactivity of antisera R521 and R568 with bovine PrP was very poor. No signal was obtained with the PK-treated material of BSE- and scrapie-negative animals. PVDF showed a higher adsorption than NC membranes since immunostaining could be observed at higher dilutions on PVDF. The detection limit of the test with sheep recombinant PrP spotted on PVDF and using antiserum R521 or R595 is about 50 pg. Using other detection methods, however, will, of course, result in even lower detection levels. Thus far, 29 cases of BSE and 131 negative controls were examined. The performance was 100% (Table 1).

The design of one of our tests is that of a dot blot immunoassay that has an intrinsically higher sensitivity than an analogous ELISA assay in a microtiter plate, due to miniaturization within the blot and the higher binding capacity of the matrix material (nitrocellulose, PVDF) than of a smooth polysterene microtiter plate surface. Because of the divergent immunoreactivity of sheep $PrP^C$ and $PrP^{Sc}$ during denaturation, the discriminatory power for false-positive samples of our test is much higher than that of the assay of Safar and coworkers; in our assay, the signal for $PrP^C$ during denaturation in 4 M gdnSCN diminishes, whereas immuno-enhancement (with 4 M gdnHCl) takes place in the assay of Safar and coworkers. As distinct from the test of Safar and coworkers, there is no need to calibrate our assay; it can be performed within four hours and it lends itself to automation. Quantification will be with densitometric techniques. Other options for the design of our assay are an ELIFA-format combined with detection in solution of an enzyme-enhanced fluorescence or luminescence signal or time-resolved detection of lanthanide fluorescence.

TABLE 1

Performance of dot-blot immunoassay on diagnosis of BSE

|  | true positive[1] | true negative[2] | total | % | 95% confidence interval[3] |
|---|---|---|---|---|---|
| positive in test | 29 | 0 | 29 |  |  |
| negative in test | 0 | 131 | 131 |  |  |
| totals | 29 | 131 | 160 |  |  |
| sensitivity |  |  |  | 100 | 89.7-100 |
| specificity |  |  |  | 100 | 97.3-100 |

[1](Immuno)histochemically confirmed cases from five different countries.
[2]All confirmed negative. These 131 negative controls consisted of 45 cows suspected of BSE and 86 cows from a herd with a BSE-case. Likewise, the performance in the case of scrapie with samples of sheep is 100% (5 positive and 5 negative cases).
[3]According to Blyth-Still-Casella.

REFERENCES

Beekes M., E. Baldauf, S. Cabens, H. Diringer, P. Keyes, A. C. Scott, A. H. Wells, P. Brown, C. J. Gibbs Jr. and D. C. Gajdusek (1995). Western blot mapping of disease-specific amyloid in various animal species and humans with transmissible spongiform encephalopathies using a high-yield purification method. *J. Gen. Virol.* 76:2567-2576.

Belt P. B. F. M., I. Muileman, B. E. C. Schreuder, J. Bos-de Ruijter, A. L. J. Gielkens and M. A. Smits (1995). Identification of five allelic variants of the sheep PrP gene and their association with natural scrapie. *J. Gen. Virol.* 76:509-517.

Bell J. E., S. M. Gentleman, J. W. Ironside, L. Mccardle, P. L. Lantos, L. Doey, J. Lowe, J. Ferguson, P. Luthert, S. McQuaid and I. V. Allen (1997). Prion protein immunocytochemistry—UK five centre consensus report. *Neuropath. Appl. Neurobiol.* 23:26-35.

Billeter M., R. Riek, G. Wider, S. Hornemann, R. Glockshuber and K. Wilthrich (1997). Prion protein NMR structure and species barrier for prion diseases. *Proc. Natl. Acad. Sci. USA* 94:7281-7285.

Bossers A., B. E. C. Schreuder, I. H. Muileman, P. B. G. M. Belt and M. A. Smits (1996). PrP genotype contributes to determining survival times of sheep with natural scrapie. *J. Gen. Virol.* 77:2669-2673.

Bradley et al. (1994). European Commission, Directorate General for Agriculture, Unit for Veterinary Legislation and Zootechnics, Protocols for the laboratory diagnosis and confirmation of bovine spongiform encephalopathy and scrapie. *Report from the Scientific Veterinary Committee.*

Bruce M. E. and H. Fraser (1991). Scrapie strain variation and implications. In: B. Chesebro (ed.). Transmissible spongiform encephalopathies. *Current Topics Microbiol. Immunol.* 172:125-138.

Bruce M. E., R. G. Will, J. W. Ironside, I. McConnell, D. Drummond, A. Suttle, L. McCardle, A. Chree, J. Hope, C. Birkett, S. Cousens, H. Fraser and C. J. Bostock (1997). Transmissions to mice indicate that "new variant" CJD is caused by the BSE agent. *Nature* 389:498-501.

Caughey B. and G. J. Raymond (1991). The scrapie-associated form of PrP is formed from a cell surface precursor that is both protease- and phospholipase-sensitive. *J. Biol. Chem.* 266:18217-18223.

Collinge J., K. C. L. Sidle, J. Meads, J. Ironside and A. F. Hill (1996). Molecular analysis of prion strain variation and the aetiology of "new variant" CJD. *Nature* 383:685-690.

Donne D. G., J. H. Viles, D. Groth, I. Mehlhom, T. L. James, F. E. Cohen, S. B. Prusiner, P. E. Wright and H. J. Dyson (1997). Structure of the recombinant full-length hamster prion protein PrP(29-131): the N terminus is highly flexible. *Proc. Natl. Acad. Sci. U.S.A.* 94:13452-13457.

Foster J., J. Hope and H. Fraser (1993). Transmission of bovine spongiform encephalopathy to sheep and goats. *Vet. Rec.* 133:339-341.

Gibbs C. J. Jr., J. Safar, M. Ceroni, A. DiMartino, W. W. Clark and J. L. Hourrigan (1990). Experimental transmission of scrapie to cattle. *Lancet* 335:1275.

Grathwohl K.-U. D., M. Horiuchi, N. Ishiguro and M. Shinagawa (1997). Sensitive enzyme-linked immunosorbent assay for detection of $PrP^{Sc}$ in crude tissue extracts from scrapie-affected mice. *J. Virol. Meth.* 64:205-216.

Hourrigan J. L. (1990). Experimentally induced bovine spongiform encephalopathy in cattle in Mission, Tex., and the control of scrapie. *J. Am. Vet. Med. Assoc.* 196:1678-1679.

Hunter N., W. Goldmann, G. Smith and J. Hope (1994). The association of a codon 136 PrP gene variant with the occurrence of natural scrapie. *Arch. of Virol.* 137:171-177.

Ikegami Y., M. Ito, H. Isomura, E. Momotani, K. Sasaki, Y. Muramatsu, N. Ishiguro and M. Shinagawa (1991). Preclinical and clinical diagnosis of scrapie by detection of PrP protein in tissues of sheep. *Vet Rec.* 128:271-275.

Kaszsak R. J., R. Rubenstein, P. A. Merz, M. Tonna-DeMasi, R. Fersko, R. I. Carp, H. M. Wisniewski and H. Diringer (1987). Mouse polyclonal and monoclonal antibody to scrapie-associated fibril proteins. *J. Virol.* 61:3688-3693.

Korth C., B. Stierli, P. Streit, M. Moser, O, Schaller, R. Fischer, W. Schulz-Schaeffer, H. Kretzschmar, A. Raeber, U. Braun, F. Ehrensperger, S. Homemann, R. Glockshuber, R. Riek, M. Billeter, K. Wüthrich and B. Oesch (1997). Prion $PrP^{Sc}$-specific epitope defined by a monoclonal antibody. *Nature* 390:74-77.

Laplanche J. L., J. Chatelain, D. Westaway, S. Thomas, M. Dussausy, J. Brugere-Picoux and J. M. Launay (1993). PrP polymorphism associated with natural scrapie discovered by denaturing gradient gel electrophoresis. *Genomics* 15:30-37.

Mehlhorn I., D. Groth, J. Stöckel, B. Moffat, D. Reilly, D. Yansura, W. S. Willett, M. Baldwin, R. Fletterick, F. E. Cohen, R. Vandlen, D. Henner and S. B. Prusiner (1996). High-level expression and characterization of a purified 142-residue polypeptide of the prion protein. *Biochemistry* 35:5528-5537.

Muramatsu Y., A. Onodera, M. Horiuchi, N. Ishiguro and M. Shinagawa (1994). Detection of PrPres in sheep at the preclinical stage of scrapie and its significance for diagnosis of insidious infection. *Arch. Virol.* 134:427-432.

Oesch B., M. Jensen, P. Nilsson and J. Fogh (1994). Properties of the scrapie prion protein: quantitative analysis of protease resistance. *Biochemistry* 33:5926-5931.

Pan K.-M., N. Stahl and S. B. Prusiner (1992). Purification and properties of the cellular prion protein from Syrian hamster brain. *Protein Science* 1:1343-1352.

Pan K.-M., M. Baldwin, J. Nguyen, M. Gasset, A. Serban, D. Groth, I. Mehlhorn, Z. Huang, R. J. Fletterick, F. E. Cohen and S. B. Prusiner (1993). Conversion of alpha-helices into beta-sheets features in the formation of the scrapie prion proteins. *Proc. Natl. Acad. Sci. U.S.A.* 90:10962-10966.

Pattison I. H. (1988). Fifty years with scrapie: a personal reminiscence. *Vet. Rec.* 123:661-666.

Prusiner S. B., M. Scott, D. Foster, K.-M. Pan, D. Groth, C. Mirenda, M. Torchia, S.-L. Yang, D. Serban, G. A. Carlson, P. C. Hoppe, D. Westaway and S. J. DeArmond (1990). Transgenetic studies implicate interactions between homologous PrP isoforms in scrapie prion replication. *Cell* 63:673-686.

Prusiner S. B., M. R. Scott, S. J. DeArmond and F. E. Cohen (1998). Prion protein biology. *Cell* 93:337-348.

Race R. E., D. Ernst, A. Jenny, W. Taylor, D. Sutton and B. Caughey (1992). Diagnostic implications of detection of proteinase K-resistant protein in spleen, lymph nodes, and brain of sheep. *Am. J. Vet. Res.* 53:883-889.

Riek R., S. Homemann, G. Wider, M. Billeter, R. Glockshuber and K. Wüthrich (1996). NMR-structure of the mouse prion protein domain PrP (121-231). *Nature* 382:180-182.

Riek R., S. Homemann, G. Wider, R. Glockshuber and K. Wüthrich (1997). NMR characterization of the full-length recombinant murine prion protein, mPrP (23-231). *FEBS Lett.* 413:282-288.

Safar J., H. Wille, V. Itri, D. Groth, H. Serban, M. Torchia, F. E. Cohen and S. B. Prusiner (1998). Eight prion strains have PrP$^{Sc}$ molecules with different conformations. *Nature Medicine* 4(10):1157-1165.

Schatzl H. M., M. Da Costa, L. Taylor, F. E. Cohen and S. B. Prusiner (1995). Prion protein gene variation among primates. *J. Mol. Biol.* 245:362-347.

Schmerr M. J., K. R. Goodwin, R. C. Cutlip and A. L. Jenny (1995). A competition assay to detect scrapie prion protein by capillary electrophoresis. *J Microcolumn Separations* 7:521-527.

Schmerr M. J., K. R. Goodwin, R. C. Cutlip and A. L. Jenny (1996). Improvements in a competition assay to detect scrapie prion protein by capillary electrophoresis. *J. Chromatog. B* 681:29-35.

Schmerr M. J. and A. Jenny (1998). A diagnostic test for scrapie-infected sheep using a capillary electrophoresis immunoassay with fluorescence-labeled peptides. *Electrophoresis* 19:409-414.

Schreuder B. E. C., L. J. M. van Keulen, M. E. W. Vromans, J. P. M. Langeveld and M. A. Smits (1996). Preclinical test for prion diseases. Nature 381:563.

Schreuder B. E. C., L. J. M. van Keulen, M. E. W. Vromans, J. P. M. Langeveld and M. A. Smits (1998). Tonsillar biopsy and PrP$^{Sc}$ detection in the preclinical diagnosis of scrapie. *Vet. Rec.* 142:564-568.

Serban D., A. Taraboulos, S. J. DeArmond and S. B. Prusiner (1990). Rapid detection of Creutzfeldt-Jakob disease and scrapie prion proteins. *Neurology* 40:110-117.

Van Keulen L. J. M., B. E. C. Schreuder, R. H. Meloen, G. Mooij-Harkes, M. Poelen-van den Berg, M. E. W. Vromans and J. P. M. Langeveld (1995). Immunohistochemical detection and localization of prion protein in brain tissue of sheep with natural scrapie. *Vet. Pathol.* 32:299-308.

Van Keulen L. J. M., B. E. C. Schreuder, R. H. Meloen, G. Mooij-Harkes, M. E. W. Vromans and J. P. M. Langeveld (1996). Immunohistochemical detection of prion protein in lymphoid tissues of sheep with natural scrapie. *J. Clin. Microbiol.* 34:1228-1231.

Wilesmith J. W., J. B. M. Ryan and M. J. Atkinson (1991). Bovine spongiform encephalopathy: epidemiological studies on the origin. *Vet. Rec.* 128:199-203.

Will R. G., J. W. Ironside, M. Zeidler, S. N. Cousens, K. Estibeiro, A. Alperovitch, S. Poser, M. Pocchiari, A. Hofman and P. G. Smith (1996). A new variant of Creutzfeldt-Jakob disease in the UK. *Lancet* 347:921-925.

What is claimed is:

1. A method for increasing the discriminating value of a test when testing at least one sample obtained from a mammal for the presence or absence of an aberrant prion protein, the method comprising:

using said at least one sample to prepare a test set and a control set without administration of a denaturation agent;

denaturing protein in said test set with guanidine thiocyanate or one or more chaotropic agents so as to enhance antibody reactivity towards aberrant protein, while antibody reactivity towards a normal form of the protein is reduced or unchanged;

leaving said control set untreated with guanidine thiocyanate or one or more chaotropic agents;

incubating said test set and said control set with anti-PrP$^{Sc}$ antibodies;

probing said test set and said control set for the presence or absence of an aberrant prion protein; and determining with said anti-PrP$^{Sc}$ antibodies instances of increased antibody reactivity as a function of denaturation in guanidine thiocyanate or one or more chaotropic agents in the test set versus the control set.

2. The method according to claim 1, wherein said at least one sample is tested in an immunoassay.

3. The method according to claim 1, further comprising treating said at least one sample with a protease to reduce the presence of normal prion protein.

4. The method according to claim 1, wherein said mammal is a ruminant.

5. The method according to claim 4, wherein said ruminant is ovine or bovine.

6. The method according to claim 1, further comprising immunologically detecting said aberrant prion protein with at least one antibody directed against a proteinase K-resistant part of the aberrant prion protein.

7. The method according to claim 6, wherein said at least one antibody is directed against a proteinase K-resistant N-terminal part of the aberrant prion protein.

8. The method according to claim 1, wherein said at least one antibody is raised against an epitope from the aberrant prion protein.

9. The method according to claim 8, wherein said epitope has a sequence selected from the group consisting of SEQ ID NOS:7-30.

10. The method according to claim 6, wherein said aberrant prion protein is immunologically detected in an enzyme-linked immunoassay.

11. A method for reducing the risk of scoring a false-positive test result when testing at least one sample obtained from a mammal for the presence or absence of an aberrant prion protein, the method comprising:

using said at least one sample to prepare a test set and a control set without administration of a denaturation agent;

denaturing protein in said test set with guanidine thiocyanate or one or more chaotropic agents so as to enhance antibody reactivity towards aberrant protein, while antibody reactivity towards a normal form of the protein is reduced or unchanged;

leaving said control set untreated with guanidine thiocyanate or one or more chaotropic agents;

incubating said test set and said control set with anti-PrP$^{Sc}$ antibodies;

probing said test set and said control set for the presence or absence of an aberrant prion protein;

determining with said antibodies instances of increased antibody reactivity as a function of denaturation in guanidine thiocyanate or one or more chaotropic agents in the test set versus the control set; and immunologically detecting said aberrant prion protein in an enzyme-linked immunoassay, wherein said enzyme-linked immunoassay comprises a dot-blot assay.

* * * * *

SEQUENCE LISTING

```
<160> NUMBER OF SEQ ID NOS: 30

<210> SEQ ID NO 1
<211> LENGTH: 253
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190
```

```
Thr Lys Gly Glu Asn Phe Thr Glu Thr Asp Val Lys Met Met Glu Arg
            195                 200                 205

Val Val Glu Gln Met Cys Ile Thr Gln Tyr Glu Arg Glu Ser Gln Ala
        210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
            245                 250
```

<210> SEQ ID NO 2
<211> LENGTH: 252
<212> TYPE: PRT
<213> ORGANISM: Oryctolagus cuniculus

<400> SEQUENCE: 2

```
Met Ala His Leu Gly Tyr Trp Met Leu Leu Leu Phe Val Ala Thr Trp
1               5                   10                  15

Ser Asp Val Gly Leu Cys Lys Lys Arg Pro Lys Pro Gly Gly Gly Trp
            20                  25                  30

Asn Thr Gly Gly Ser Arg Tyr Pro Gly Gln Ser Ser Pro Gly Gly Asn
        35                  40                  45

Arg Tyr Pro Pro Gln Gly Gly Trp Gly Gln Pro His Gly Gly Gly
 50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Thr His Asn
            85                  90                  95

Gln Trp Gly Lys Pro Ser Lys Pro Lys Thr Ser Met Lys His Val Ala
            100                 105                 110

Gly Ala Ala Ala Ala Gly Ala Val Val Gly Gly Leu Gly Gly Tyr Met
            115                 120                 125

Leu Gly Ser Ala Met Ser Arg Pro Leu Ile His Phe Gly Asn Asp Tyr
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Ser Phe Val His
                165                 170                 175

Asp Cys Val Asn Ile Thr Val Lys Gln His Thr Val Thr Thr Thr Thr
            180                 185                 190

Lys Gly Glu Asn Phe Thr Glu Thr Asp Ile Lys Ile Met Glu Arg Val
            195                 200                 205

Val Glu Gln Met Cys Ile Thr Gln Tyr Gln Glu Ser Gln Ala Ala
        210                 215                 220

Tyr Gln Arg Ala Ala Gly Val Leu Leu Phe Ser Ser Pro Pro Val Ile
225                 230                 235                 240

Leu Leu Ile Ser Phe Leu Ile Phe Leu Ile Val Gly
            245                 250
```

<210> SEQ ID NO 3
<211> LENGTH: 254
<212> TYPE: PRT
<213> ORGANISM: Syrian golden hamster

<400> SEQUENCE: 3

```
Met Ala Asn Leu Ser Tyr Trp Leu Leu Ala Leu Phe Val Ala Met Trp
1               5                   10                  15
```

```
Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
             35                  40                  45

Tyr Pro Pro Gln Gly Gly Thr Trp Gly Gln Pro His Gly Gly Gly
 50                  55                  60

Trp Gly Gln Pro His Gly Gly Trp Gly Gln Pro His Gly Gly Gly
 65                  70                  75                  80

Trp Gly Gln Pro His Gly Gly Trp Gly Gln Gly Gly Gly Thr His
             85                  90                  95

Asn Gln Trp Asn Lys Pro Ser Lys Pro Lys Thr Asn Met Lys His Met
             100                 105                 110

Ala Gly Ala Ala Ala Ala Gly Ala Val Val Gly Gly Leu Gly Gly Tyr
             115                 120                 125

Met Leu Gly Ser Ala Met Ser Arg Pro Met Met His Phe Gly Asn Asp
 130                 135                 140

Trp Glu Asp Arg Tyr Tyr Arg Glu Asn Met Asn Arg Tyr Pro Asn Gln
 145                 150                 155                 160

Val Tyr Tyr Arg Pro Val Asp Gln Tyr Asn Asn Gln Asn Asn Phe Val
             165                 170                 175

His Asp Cys Val Asn Ile Thr Ile Lys Gln His Thr Val Thr Thr Thr
             180                 185                 190

Thr Lys Gly Glu Asn Phe Thr Glu Thr Asp Ile Lys Ile Met Glu Arg
             195                 200                 205

Val Val Glu Gln Met Cys Thr Thr Gln Tyr Gln Lys Glu Ser Gln Ala
             210                 215                 220

Tyr Tyr Asp Gly Arg Arg Ser Ser Ala Val Leu Phe Ser Ser Pro Pro
 225                 230                 235                 240

Val Ile Leu Leu Ile Ser Phe Leu Ile Phe Leu Met Val Gly
             245                 250

<210> SEQ ID NO 4
<211> LENGTH: 254
<212> TYPE: PRT
<213> ORGANISM: Murinae gen. sp.

<400> SEQUENCE: 4

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
             35                  40                  45

Tyr Pro Pro Gln Gly Gly Thr Trp Gly Gln Pro His Gly Gly Gly Trp
 50                  55                  60

Gly Gln Pro His Gly Gly Ser Trp Gly Gln Pro His Gly Gly Ser Trp
 65                  70                  75                  80

Gly Gln Pro His Gly Gly Trp Gly Gln Gly Gly Gly Thr His Asn
             85                  90                  95

Gln Trp Asn Lys Pro Ser Lys Pro Lys Thr Asn Leu Lys His Val Ala
             100                 105                 110

Gly Ala Ala Ala Ala Gly Ala Val Val Gly Gly Leu Gly Gly Tyr Met
             115                 120                 125

Leu Gly Ser Ala Met Ser Arg Pro Met Ile His Phe Gly Asn Asp Trp
 130                 135                 140
```

```
Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Phe Val His
            165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
            245                 250

<210> SEQ ID NO 5
<211> LENGTH: 256
<212> TYPE: PRT
<213> ORGANISM: Bos taurus

<400> SEQUENCE: 5

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Gly Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
            130                 135                 140

Gly Ser Asp Tyr Glu Asp Arg Tyr Tyr Arg Glu Asn Met His Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Glu His Thr Val
            180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
            245                 250                 255
```

<210> SEQ ID NO 6
<211> LENGTH: 256
<212> TYPE: PRT
<213> ORGANISM: Ovis aries

<400> SEQUENCE: 6

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Arg Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 7
<211> LENGTH: 13
<212> TYPE: PRT
<213> ORGANISM: Homo sapiens

<400> SEQUENCE: 7

Gly Gln Gly Gly Gly Thr His Ser Gln Trp Asn Lys Pro
1               5                   10

<210> SEQ ID NO 8
<211> LENGTH: 12
<212> TYPE: PRT
<213> ORGANISM: Oryctolagus cuniculus

<400> SEQUENCE: 8

Gly Gln Gly Gly Thr His Asn Gln Trp Gly Lys Pro
1               5                   10

<210> SEQ ID NO 9

```
<211> LENGTH: 13
<212> TYPE: PRT
<213> ORGANISM: Syrian golden hamster

<400> SEQUENCE: 9

Gly Gln Gly Gly Gly Thr His Asn Gln Trp Asn Lys Pro
1               5                   10

<210> SEQ ID NO 10
<211> LENGTH: 12
<212> TYPE: PRT
<213> ORGANISM: Bos taurus

<400> SEQUENCE: 10

Gly Gln Gly Gly Thr His Gly Gln Trp Asn Lys Pro
1               5                   10

<210> SEQ ID NO 11
<211> LENGTH: 12
<212> TYPE: PRT
<213> ORGANISM: Ovis aries

<400> SEQUENCE: 11

Gly Gln Gly Gly Ser His Ser Gln Trp Asn Lys Pro
1               5                   10

<210> SEQ ID NO 12
<211> LENGTH: 12
<212> TYPE: PRT
<213> ORGANISM: Homo sapiens

<400> SEQUENCE: 12

Ser Gln Trp Asn Lys Pro Ser Lys Pro Lys Thr Asn
1               5                   10

<210> SEQ ID NO 13
<211> LENGTH: 12
<212> TYPE: PRT
<213> ORGANISM: Oryctolagus cuniculus

<400> SEQUENCE: 13

Asn Gln Trp Gly Lys Pro Ser Lys Pro Lys Thr Ser
1               5                   10

<210> SEQ ID NO 14
<211> LENGTH: 12
<212> TYPE: PRT
<213> ORGANISM: Syrian golden hamster

<400> SEQUENCE: 14

Asn Gln Trp Asn Lys Pro Ser Lys Pro Lys Thr Asn
1               5                   10

<210> SEQ ID NO 15
<211> LENGTH: 12
<212> TYPE: PRT
<213> ORGANISM: Bos taurus

<400> SEQUENCE: 15

Gly Gln Trp Asn Lys Pro Ser Lys Pro Lys Thr Asn
1               5                   10

<210> SEQ ID NO 16
<211> LENGTH: 18
<212> TYPE: PRT
```

<213> ORGANISM: Homo sapiens

<400> SEQUENCE: 16

Gly Gly Leu Gly Gly Tyr Met Leu Gly Ser Ala Met Ser Arg Pro Ile
1               5                   10                  15

Ile His

<210> SEQ ID NO 17
<211> LENGTH: 18
<212> TYPE: PRT
<213> ORGANISM: Oryctolagus cuniculus

<400> SEQUENCE: 17

Gly Gly Leu Gly Gly Tyr Met Leu Gly Ser Ala Met Ser Arg Pro Leu
1               5                   10                  15

Ile His

<210> SEQ ID NO 18
<211> LENGTH: 18
<212> TYPE: PRT
<213> ORGANISM: Syrian golden hamster

<400> SEQUENCE: 18

Gly Gly Leu Gly Gly Tyr Met Leu Gly Ser Ala Met Ser Arg Pro Met
1               5                   10                  15

Met His

<210> SEQ ID NO 19
<211> LENGTH: 18
<212> TYPE: PRT
<213> ORGANISM: Murinae gen. sp.

<400> SEQUENCE: 19

Gly Gly Leu Gly Gly Tyr Met Leu Gly Ser Ala Met Ser Arg Pro Met
1               5                   10                  15

Ile His

<210> SEQ ID NO 20
<211> LENGTH: 18
<212> TYPE: PRT
<213> ORGANISM: Bos taurus

<400> SEQUENCE: 20

Gly Gly Leu Gly Gly Tyr Met Leu Gly Ser Ala Met Ser Arg Pro Leu
1               5                   10                  15

Ile His

<210> SEQ ID NO 21
<211> LENGTH: 33
<212> TYPE: PRT
<213> ORGANISM: Homo sapiens

<400> SEQUENCE: 21

Gly Ser Asp Tyr Glu Asp Arg Tyr Tyr Arg Glu Asn Met His Arg Tyr
1               5                   10                  15

Pro Asn Gln Val Tyr Tyr Arg Pro Met Asp Glu Tyr Ser Asn Gln Asn
                20                  25                  30

Asn

<210> SEQ ID NO 22

```
<211> LENGTH: 33
<212> TYPE: PRT
<213> ORGANISM: Oryctolagus cuniculus

<400> SEQUENCE: 22

Gly Asn Asp Tyr Glu Asp Arg Tyr Tyr Arg Glu Asn Met Tyr Arg Tyr
1               5                   10                  15

Pro Asn Gln Val Tyr Tyr Arg Pro Val Asp Gln Tyr Ser Asn Gln Asn
            20                  25                  30

Ser

<210> SEQ ID NO 23
<211> LENGTH: 33
<212> TYPE: PRT
<213> ORGANISM: Syrian golden hamster

<400> SEQUENCE: 23

Gly Asn Asp Trp Glu Asp Arg Tyr Tyr Arg Glu Asn Met Asn Arg Tyr
1               5                   10                  15

Pro Asn Gln Val Tyr Tyr Arg Pro Val Asp Gln Tyr Asn Asn Gln Asn
            20                  25                  30

Asn

<210> SEQ ID NO 24
<211> LENGTH: 33
<212> TYPE: PRT
<213> ORGANISM: Murinae gen. sp.

<400> SEQUENCE: 24

Gly Asn Asp Trp Glu Asp Arg Tyr Tyr Arg Glu Asn Met Tyr Arg Tyr
1               5                   10                  15

Pro Asn Gln Val Tyr Tyr Arg Pro Val Asp Gln Tyr Ser Asn Gln Asn
            20                  25                  30

Asn

<210> SEQ ID NO 25
<211> LENGTH: 33
<212> TYPE: PRT
<213> ORGANISM: Bos taurus

<400> SEQUENCE: 25

Gly Ser Asp Tyr Glu Asp Arg Tyr Tyr Arg Glu Asn Met His Arg Tyr
1               5                   10                  15

Pro Asn Gln Val Tyr Tyr Arg Pro Val Asp Gln Tyr Ser Asn Gln Asn
            20                  25                  30

Asn

<210> SEQ ID NO 26
<211> LENGTH: 33
<212> TYPE: PRT
<213> ORGANISM: Ovis aries

<400> SEQUENCE: 26

Gly Asn Asp Tyr Glu Asp Arg Tyr Tyr Arg Glu Asn Met Tyr Arg Tyr
1               5                   10                  15

Pro Asn Gln Val Tyr Tyr Arg Pro Val Asp Arg Tyr Ser Asn Gln Asn
            20                  25                  30

Asn
```

```
<210> SEQ ID NO 27
<211> LENGTH: 11
<212> TYPE: PRT
<213> ORGANISM: Homo sapiens

<400> SEQUENCE: 27

Arg Glu Ser Gln Ala Tyr Tyr Gln Arg Gly Ser
1               5                   10

<210> SEQ ID NO 28
<211> LENGTH: 10
<212> TYPE: PRT
<213> ORGANISM: Oryctolagus cuniculus

<400> SEQUENCE: 28

Gln Glu Ser Gln Ala Ala Tyr Gln Arg Ala
1               5                   10

<210> SEQ ID NO 29
<211> LENGTH: 12
<212> TYPE: PRT
<213> ORGANISM: Syrian golden hamster

<400> SEQUENCE: 29

Lys Glu Ser Gln Ala Tyr Tyr Asp Gly Arg Arg Ser
1               5                   10

<210> SEQ ID NO 30
<211> LENGTH: 12
<212> TYPE: PRT
<213> ORGANISM: Bos taurus

<400> SEQUENCE: 30

Arg Glu Ser Gln Ala Tyr Tyr Gln Arg Gly Ala Ser
1               5                   10
```